(12) United States Patent
Pierce

(10) Patent No.: US 6,669,720 B1
(45) Date of Patent: *__Dec. 30, 2003__

(54) PROSTHESIS FOR ENDOVASCULAR REPAIR OF ABDOMINAL AORTIC ANEURYSMS

(76) Inventor: George E. Pierce, 270 Lakeshore West, Lake Quivira, KS (US) 66106

( * ) Notice: Subject to any disclaimer, the term of this patent is extended or adjusted under 35 U.S.C. 154(b) by 19 days.

This patent is subject to a terminal disclaimer.

(21) Appl. No.: 09/717,532

(22) Filed: Nov. 21, 2000

Related U.S. Application Data

(63) Continuation of application No. 09/014,012, filed on Jan. 27, 1998, now Pat. No. 6,152,956.
(60) Provisional application No. 60/036,016, filed on Jan. 28, 1997.

(51) Int. Cl.[7] .................................................. A61F 2/06
(52) U.S. Cl. ..................................... 623/1.13; 623/1.36
(58) Field of Search ............................... 623/1.13, 1.36, 623/1.16

(56) References Cited

U.S. PATENT DOCUMENTS

| | | | |
|---|---|---|---|
| 3,657,744 A | * | 4/1972 | Ersek .......................... 128/898 |
| 5,360,443 A | * | 11/1994 | Barone et al. ............. 623/1.36 |
| 5,387,235 A | | 2/1995 | Chuter |
| 5,397,345 A | | 3/1995 | Lazarus |
| 5,456,713 A | | 10/1995 | Chuter |
| 5,464,449 A | | 11/1995 | Ryan et al. |
| 5,489,295 A | | 2/1996 | Piplani et al. |
| 5,507,769 A | | 4/1996 | Marin et al. |
| 5,522,880 A | | 6/1996 | Barone et al. |
| 5,562,726 A | | 10/1996 | Chuter |
| 5,562,728 A | | 10/1996 | Lazarus et al. |
| 5,571,167 A | | 11/1996 | Maginot |
| 5,571,170 A | | 11/1996 | Palmaz et al. |
| 5,571,171 A | | 11/1996 | Barone et al. |
| 5,578,072 A | | 11/1996 | Barone et al. |
| 5,591,197 A | | 1/1997 | Orth et al. |
| 5,591,228 A | | 1/1997 | Edoga |
| 5,591,229 A | | 1/1997 | Parodi |
| 5,609,625 A | | 3/1997 | Piplani et al. |
| 5,609,627 A | * | 3/1997 | Goicoechea et al. ....... 623/1.36 |
| 5,609,628 A | | 3/1997 | Keranen |
| 5,628,783 A | | 5/1997 | Quiachon et al. |
| 5,643,208 A | | 7/1997 | Parodi |

(List continued on next page.)

FOREIGN PATENT DOCUMENTS

| | | |
|---|---|---|
| RU | 1457-921 | 2/1989 |
| SU | 1457921 A1 | 2/1989 |

OTHER PUBLICATIONS

Blum, U. et al., "Abdominal aortic aneurysms: preliminary technical and clinical results . . . ", *Radiology* 198(1):25–31 (Jan. 1996).

Blum, U. et al., "Endoluminal stent–grafts for infrarenal abdominal aortic aneurysms", (Name of publication unknown), 336(1):13–20 (Jan. 2, 1997).

Chuter, T. et al., "Transfemoral endovascular aortic graft placement", *Journal of Vascular Surgery* 18(2):185–197 (Aug. 1993).

(List continued on next page.)

*Primary Examiner*—David H. Willse
*Assistant Examiner*—Javier G. Blanco
(74) *Attorney, Agent, or Firm*—Merchant & Gould P.C.

(57) ABSTRACT

An apparatus for endovascular repair of aortic aneurysms is disclosed. In one form, the apparatus includes a tube and an anchoring unit that includes a plurality of thin lines. The tube serves as a conduit for blood flow in an aneurysm of an aorta. A first end of the plurality of lines is connected to a first end of the tube. A second end of the plurality of lines is separated by a distance from the first end of the tube for anchoring the apparatus at a location away from the aneurysm.

13 Claims, 10 Drawing Sheets

U.S. PATENT DOCUMENTS

| | | | |
|---|---|---|---|
| 5,662,700 A | | 9/1997 | Lazarus |
| 5,662,702 A | | 9/1997 | Keranen |
| 5,669,936 A | | 9/1997 | Lazarus |
| 5,676,697 A | | 10/1997 | McDonald |
| 5,683,449 A | | 11/1997 | Marcade |
| 5,695,517 A | | 12/1997 | Marin et al. |
| 5,713,917 A | * | 2/1998 | Leonhardt et al. .......... 623/1.36 |
| 5,755,773 A | | 5/1998 | Evans et al. |
| 5,769,887 A | * | 6/1998 | Brown et al. ............... 623/1.36 |
| 5,824,039 A | | 10/1998 | Piplani et al. |
| 6,004,347 A | * | 12/1999 | McNamara et al. ........ 623/1.36 |
| 6,102,938 A | | 8/2000 | Evans et al. |
| 6,102,940 A | * | 8/2000 | Robichon et al. .......... 623/1.36 |
| 6,152,956 A | * | 11/2000 | Pierce ........................ 623/1.36 |
| 6,168,610 B1 | | 1/2001 | Marin et al. |
| 6,273,909 B1 | * | 8/2001 | Kugler et al. ............... 623/1.36 |
| 6,290,731 B1 | * | 9/2001 | Solovay et al. ............. 623/1.16 |
| 6,344,056 B1 | * | 2/2002 | Dehdashtian ............... 623/1.35 |
| 6,409,757 B1 | * | 6/2002 | Trout, III et al. ........... 623/1.36 |
| 6,416,542 B1 | | 7/2002 | Marcade et al. |
| 6,464,721 B1 | | 10/2002 | Marcade et al. |
| 6,517,572 B2 | * | 2/2003 | Kugler et al. ............... 623/1.13 |
| 2002/0042646 A1 | * | 4/2002 | Wall ........................... 623/1.13 |

OTHER PUBLICATIONS

Cragg, A. et al., "Nitinol intravascular stent: Results of preclinical evaluation", *Radiology* 189(3):775–778 (Dec. 1993).

Moore, W. et al., "Transfemoral endovascular repair of abdominal aortic aneurysm: Results of the North American EVT phase 1 trial", *Journal of Vascular Surgery* 23(4):543–553 (Apr. 1996).

Palmaz, J. et al., "Use of stents covered with polytetrafluoroethylene in experimental abdominal aortic aneurysm", *Journal of Vascular and Interventional Radiology* 6(6):879–885 (Nov.–Dec. 1995).

Palmaz, J. et al., "Tutorial 16–Intraluminal stents: General principles", pp. 176–182 (publication and date unknown).

Parodi, J. et al., "Endovascular repair of abdominal aortic aneurysms and other arterial lesions", *Journal of Vascular Surgery* 21(4):549–557 (Apr. 1995).

Piquet, P. et al., "Tantalum–Dacron coknit stent for endovascular treatment of aortic aneurysms: A preliminary experimental study", *Journal of Vascular Surgery* 19(4):698–706 (Apr. 1994).

White, G. et al, "Three–year experience with the White–Yu endovascular GAD graft for transluminal repair of aortic and iliac aneurysms", *J Endovasc Surg* 4:124–136 (1997).

"FDA Public Health Notification: Problems with Endovascular Grafts for Treatment of Abdominal Aortic Aneurysm (AAA)," http://www.fda.gov/cdrh/safety/aaa.html, 3 pgs. (Apr. 27, 2001).

"The Facts: Abdominal Aortic Aneurysm," http://www.vascular.uams.edu/abaorticaneurysm.htm, 4 pgs, (Date Unknown).

* cited by examiner

PROSTHESIS FOR ENDOVASCULAR REPAIR OF ABDOMINAL AORTIC ANEURYSMS

RELATED APPLICATIONS

This application is a continuation of application Ser. No. 09/014,012, filed Jan. 27, 1998, now U.S. Pat. No. 6,152,956, which claims the benefit of priority of provisional application Serial No. 60/036,016, filed Jan. 28, 1997, which applications are incorporated herein by reference.

BACKGROUND OF THE INVENTION

1. Field of the Invention

The invention relates to vascular prostheses, and more particularly, to prostheses for endovascular repair of aortic aneurysms.

2. Description of Related Art

An aneurysm is a localized dilatation or weak spot in a blood vessel. Abdominal aortic aneurysms are one of the most common and serious types of aneurysm. They are thought to be atherosclerotic in origin, i.e., related toga high fat diet, high blood pressure, and cigarette smoking. But genetic factors that control collagen and/or elastic tissue metabolism may also be involved.

A common abdominal aortic aneurysm 10 is illustrated in FIG. 1. The aorta 12 is the large artery that arises directly from the heart. After it passes below the diaphragm, into the abdomen, the aorta 12 gives off major branches that supply the liver, stomach and spleen (the hepatic, left gastric and splenic arteries, the common trunk of which is the coeliac artery 14), the intestines (superior mesenteric artery 16), and the kidneys (renal arteries 18, 20). It then divides into right and left trunks 22, 24, called iliac arteries, which supply circulation to the legs.

Abdominal aortic aneurysms 10 most often develop in the relatively long segment 26 of aorta between the renal arteries 18, 20 and the bifurcation of the aorta into the right and left iliac arteries 22, 24. Abdominal aortic aneurysms 10 progressively enlarge at variable and unpredictable rates, and as they do, the involved aneurysm wall becomes weaker and thinner, and eventually ruptures. Rupture is relatively uncommon in abdominal aortic aneurysms less than five centimeters maximum transverse diameter, but the risk increases with increasing size. Rupture of abdominal aortic aneurysms causes approximately 15,000 deaths per year in the United States.

Surgery to prevent rupture is recommended for most patients with abdominal aortic aneurysms five centimeters maximum transverse diameter or greater. Presently approximately 40,000 of these operations are performed each year in the United States.

The standard operation involves a long midline incision in the abdominal wall that extends from the lower end of the sternum to the pubic bone. Blood flow through the aneurysm is temporarily stopped by occluding the aorta with a clamp placed above the aneurysm 10 and clamps placed across the right and left iliac arteries 22, 24, which are, below the aneurysm. The aneurysm 10 is opened, and a plastic fabric tube graft is anastomosed (i.e., joined) to the normal, non-dilated aorta above the aneurysm 10. The other end of the tube graft is joined to the non-dilated aorta below the aneurysm 10.

Thus, the diseased segment (i.e., aneurysm) is replaced by a plastic tube. The anastomoses (i.e., junctions) between the aorta and the graft are sewn with surgical sutures. In some patients, a bifurcated graft in place of a single tube graft must be used. These grafts are shaped like an inverted "Y". The single trunk is joined to the proximal aorta and the right and left limbs are joined distally to the right and left iliac arteries (herein the words proximal and distal are used with the heart being the point of reference). These inverted Y grafts are used in patients who have no segment of non-dilated aorta below the aneurysm.

This major operation can be performed in relatively good-risk patients with a mortality rate of less than five percent. However, the operation requires five to ten days of postoperative hospital care and a four to six week recovery period. Furthermore, the operation cannot be safely performed in many patients with severe cardiac or pulmonary impairment.

Recently, alternative methods of repair that do not involve the large, open abdominal incision have been developed. One of these is the so-called "endovascular" approach. With the endovascular approach, a small incision is made in a groin to form a small opening in one of the iliac arteries 22. A guide wire 30 (FIG. 2) is passed up through the iliac artery 22 into the aorta 12 and through the aneurysm 10, under continuous X-ray, i.e., fluoroscopic control. A soft plastic fabric tube graft 29 is placed over a metal mesh stent 31 (in its non-extended state) which is mounted over the balloon portion 32 (non-distended) of a large angioplasty type catheter 34. The fabric graft is folded longitudinally so that the entire apparatus (i.e., plastic graft, underlying stent and balloon angioplasty catheter) can be loaded into a flexible plastic sheath 33 (e.g., Teflon™) and passed into the lumen of the iliac artery 22 and up into the aneurysm 10. Once the prosthesis is properly positioned, the sheath 33 is withdrawn.

Proximal fixation of the graft is accomplished with the underlying stent. The upper end of the graft is secured by the stent to the segment of non-dilated aorta 36 just above the aneurysm 10. This segment 36 that lies above the aneurysm but below the renal arteries is sometimes referred to as the "neck" of the aneurysm (and will be referred to as such herein), although it is not actually a part of the aneurysm. After withdrawal of the delivery sheath 33, the balloon 32 is distended to expand the stent 31 so that the stent 31 presses the outer wall of the graft 29 against the inner wall of the neck 36 of the aneurysm. An alternative method of fixation involves a ring of interconnected, fine-metal hooks or barbs pre-sewn into the upper end of the graft. The metal hooks or barbs are "fired" into the wall of the neck of the aneurysm by inflation of the catheter balloon 32. Yet another known method is a combination of a stent and hooks or barbs, in which the hooks or barbs are welded to the stent.

Proper proximal fixation of the graft to the aorta is important for two reasons. One, proximal fixation prevents leaks to the outside of the graft, leaks which would maintain high arterial pressure within the abdominal aortic aneurysm and lead to progressive enlargement and rupture. Two, proximal fixation prevents distal migration and collapse of the soft plastic fabric tube graft by the force of arterial blood flow. Over time, fibrous tissue grows from the aortic wall into the interstices of the porous fabric graft providing some additional fixation.

Blood pressure and flow tend to keep the lower end of the graft expanded against the aortic wall by a so-called "parachute" effect. However, distal fixation of the graft is generally accomplished by placement of a second short, expandable metal stent similar to the stent used in the upper end. The second stent is expanded at the lower end of the graft so that the stent presses the outer wall of the graft against the inner wall of the aorta below the aneurysm.

There are several major unsolved problems with proximal fixation of endovascular grafts that limit their application in the repair of many abdominal aortic aneurysms. One such problem is that the aneurysm neck 36 is often too short to permit adequate fixation with an expandable stent. (Generally, a length of two centimeters or more is needed for adequate anchoring of the graft.) Additionally, the aneurysm neck is frequently too heavily, calcified to permit fixation with hooks, i.e., the hooks cannot penetrate areas of the aortic wall that have thick, calcified plaques. In other cases, the inner wall of the neck is thickened by soft, friable plaque or thrombus that makes fixation with hooks impossible or inadequate.

SUMMARY OF THE INVENTION

To permit wider application of endovascular repair of aortic aneurysms, and to overcome other limitations in the prior art, the present invention discloses a new apparatus for endovascular repair of aortic aneurysms. In one form, the invention comprises a prosthesis including a tube and an anchoring unit that includes a plurality of thin lines. The tube provides a conduit for blood flow through an aortic aneurysm. A first end of the plurality of lines is connected to a first end of the tube. A second end of the plurality of lines is separated by a distance from the first end of the tube for anchoring the prosthesis at a location away from the aneurysm.

In one embodiment, the prosthesis is constructed for repairing an abdominal aortic aneurysm between the renal and iliac arteries. The tube extends at least the length of the aneurysm. The plurality of lines extend from the first end of the tube to a position above the coeliac artery, where the prosthesis is anchored.

In one embodiment of the invention, the anchoring unit further includes an expandable stent connected to the second end of the plurality of lines. Furthermore, in one embodiment of the invention, the plurality of lines are curved so that the first end of the plurality of lines pushes, from a compressed state, radially outward so as to conform to the shape of an aortic wall and to exert a pressure thereon. Additionally, in one embodiment of the invention, the second end of the plurality of lines is sharp and the plurality of lines are curved so that the second end of the plurality of lines pushes, from a compressed state, radially outward so as to embed in an aortic wall to anchor the prosthesis.

The invention includes several other features and embodiments. The claims annexed hereto and forming a part hereof point out with particularity various embodiments and features of novelty which characterize the invention. The drawings and accompanying descriptive matter herein illustrate and describe specific examples of an apparatus formed in accordance with invention.

BRIEF DESCRIPTION OF THE DRAWINGS

Referring now to the drawings in which like reference numbers represent corresponding parts throughout:

FIG. 7b is a cross-sectional view taken along section line 7b—7b of FIG. 7a.

DETAILED DESCRIPTION OF PREFERRED EMBODIMENTS

Figure 1:
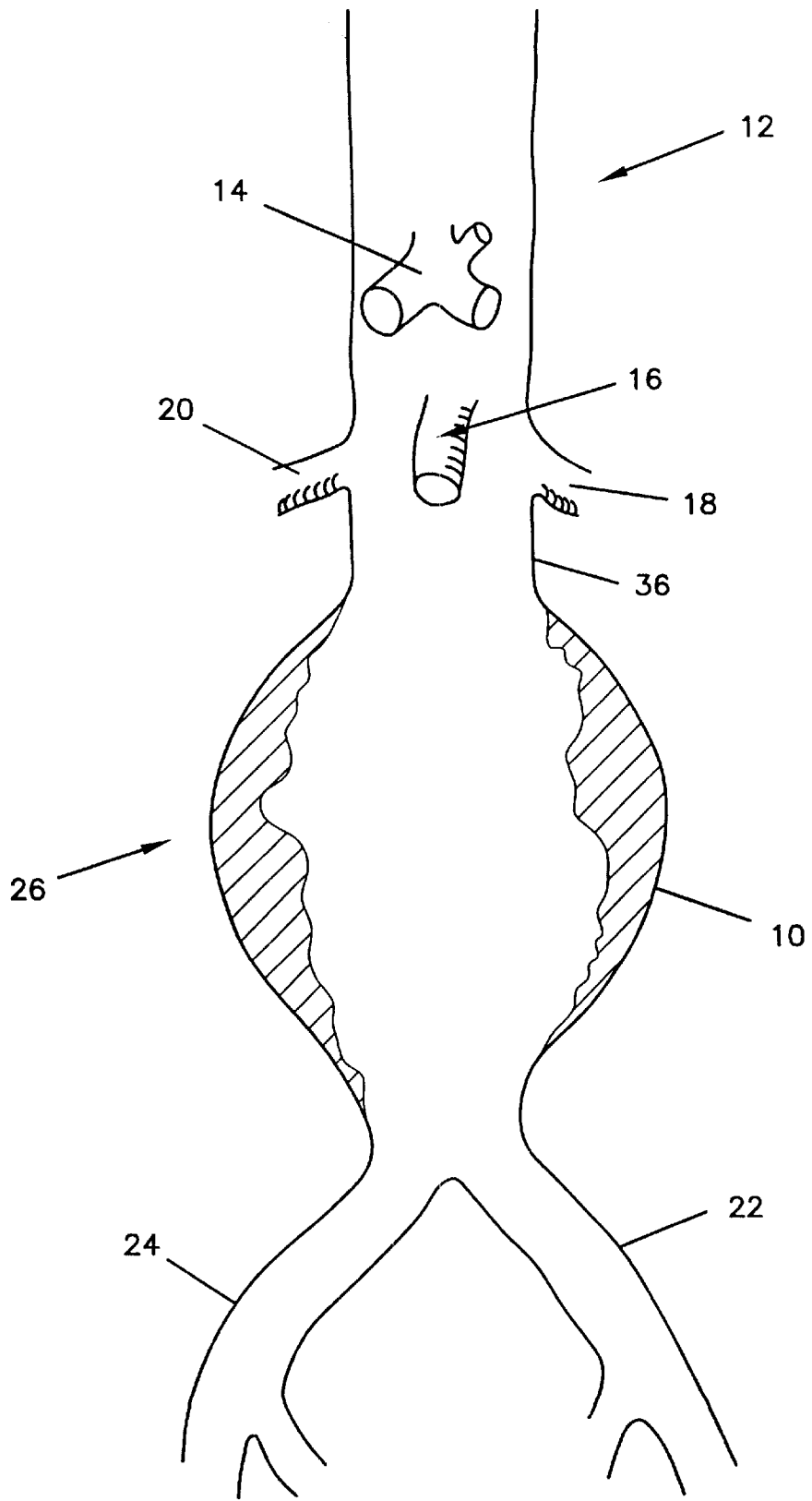
FIG. 1 is a pictorial diagram of an aneuryzmal abdominal aorta.
Figure 2:
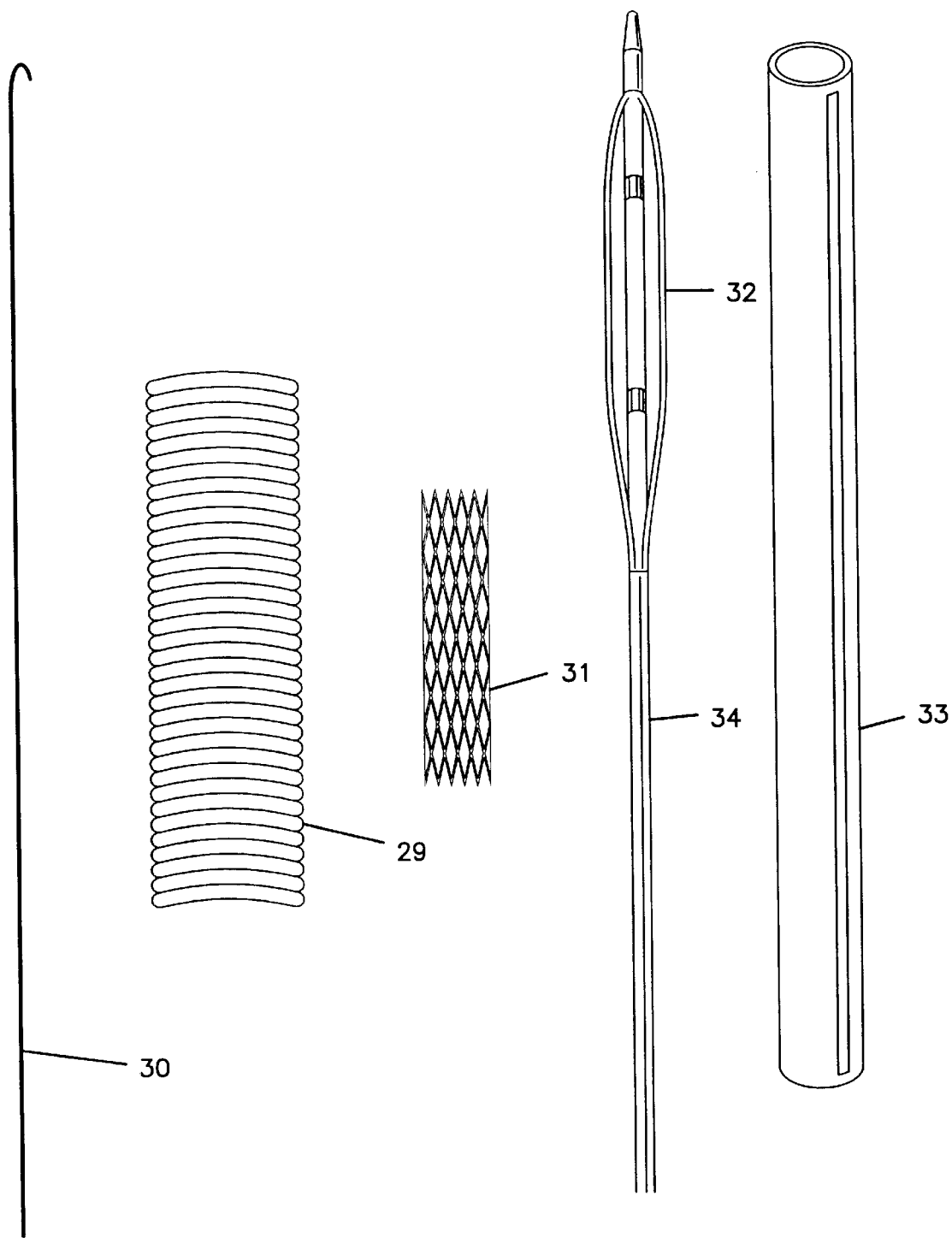
FIG. 2 is a pictorial diagram of a guide wire, a graft, a stent, a balloon catheter, and a flexible delivery sheath.
Figure 3:
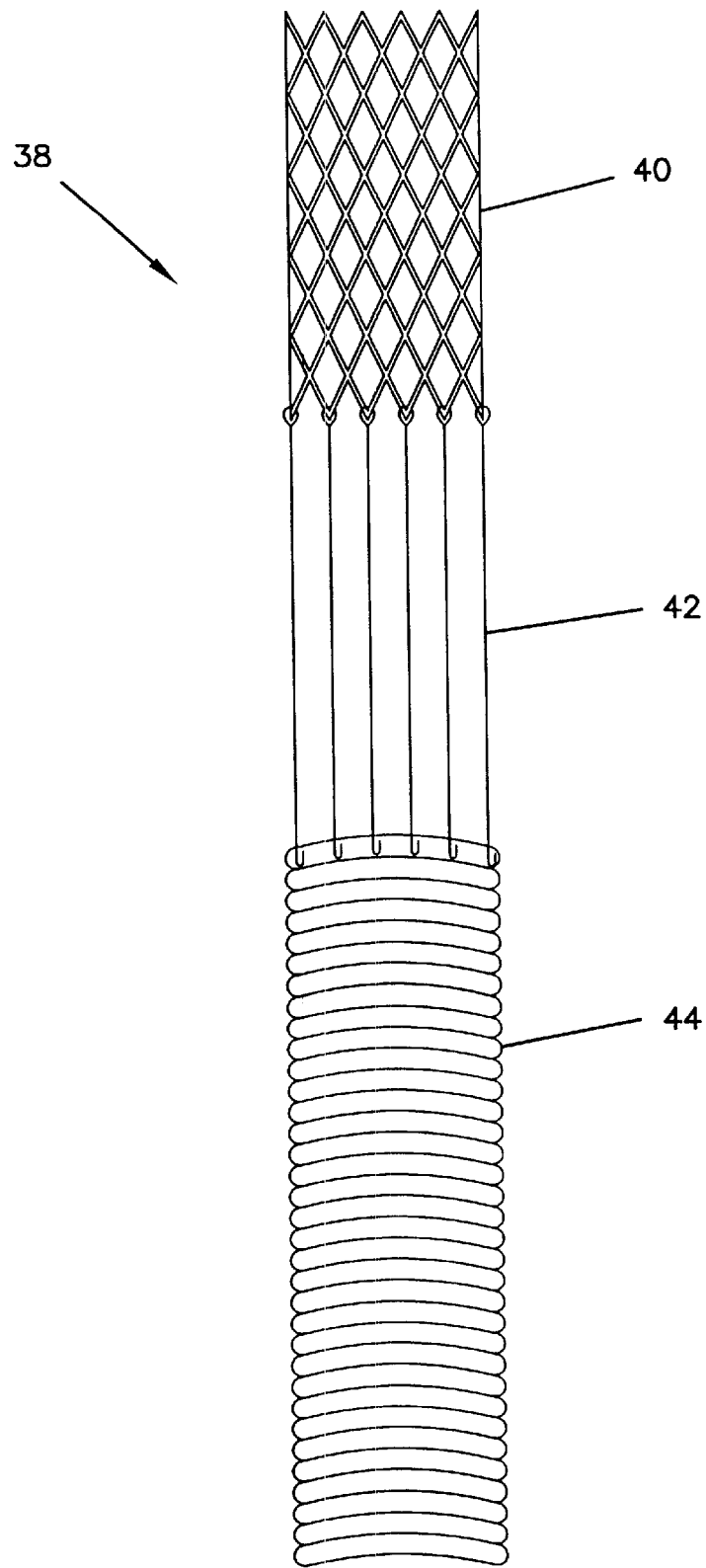
FIG. 3 is a pictorial diagram of a prosthesis formed in accordance with the invention.
Figure 4:
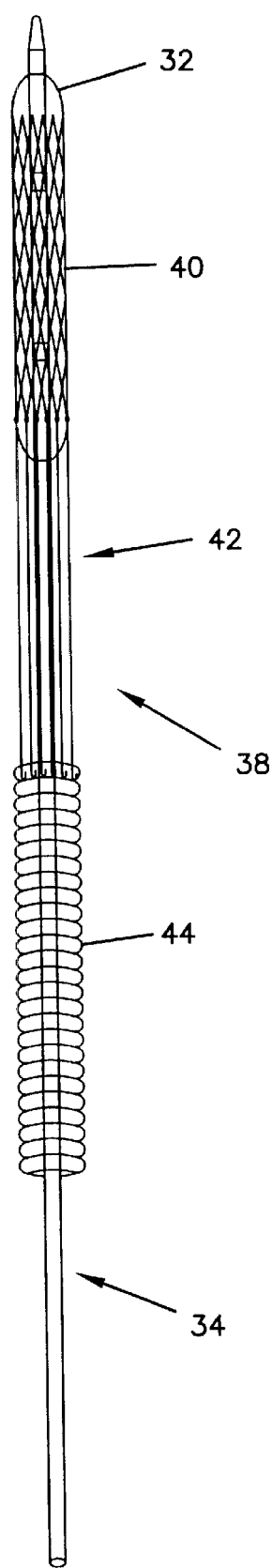
FIG. 4 is a pictorial diagram showing the prosthesis of FIG. 3 loaded on a balloon catheter in accordance with the invention.

FIG. 3 depicts one preferred embodiment of the invention. The prosthesis 38 includes an expandable stent 40 (shown in its expanded state), connecting wires 42, and a tubular graft 44. The upper ends of the connecting wires 42 are connected to the lower end of the expandable stent 40, and the lower ends of the connecting wires 42 are connected to the upper end of the graft 44. FIG. 4 depicts this embodiment of the invention loaded on a balloon catheter with the stent in its non-expanded state, as explained in greater detail below. In one preferred embodiment, a flexible, plastic sheath 33 (as illustrated in FIG. 2) is placed over the prosthesis 38 for delivery of the prosthesis. (The sheath 33 is not shown in FIG. 4.)

The connecting wires 42 and metal stent 40 allow fixing the upper end of the prosthesis 38 to a segment of aorta that is separate and apart from the aortic position of the graft 44 itself. Thus, fixation can be made at a segment of the aorta that is much better suited for anchoring the graft because, e.g., it is much less frequently and severely diseased and is greater in length than the diseased "neck" of the aneurysm.

Figure 5:
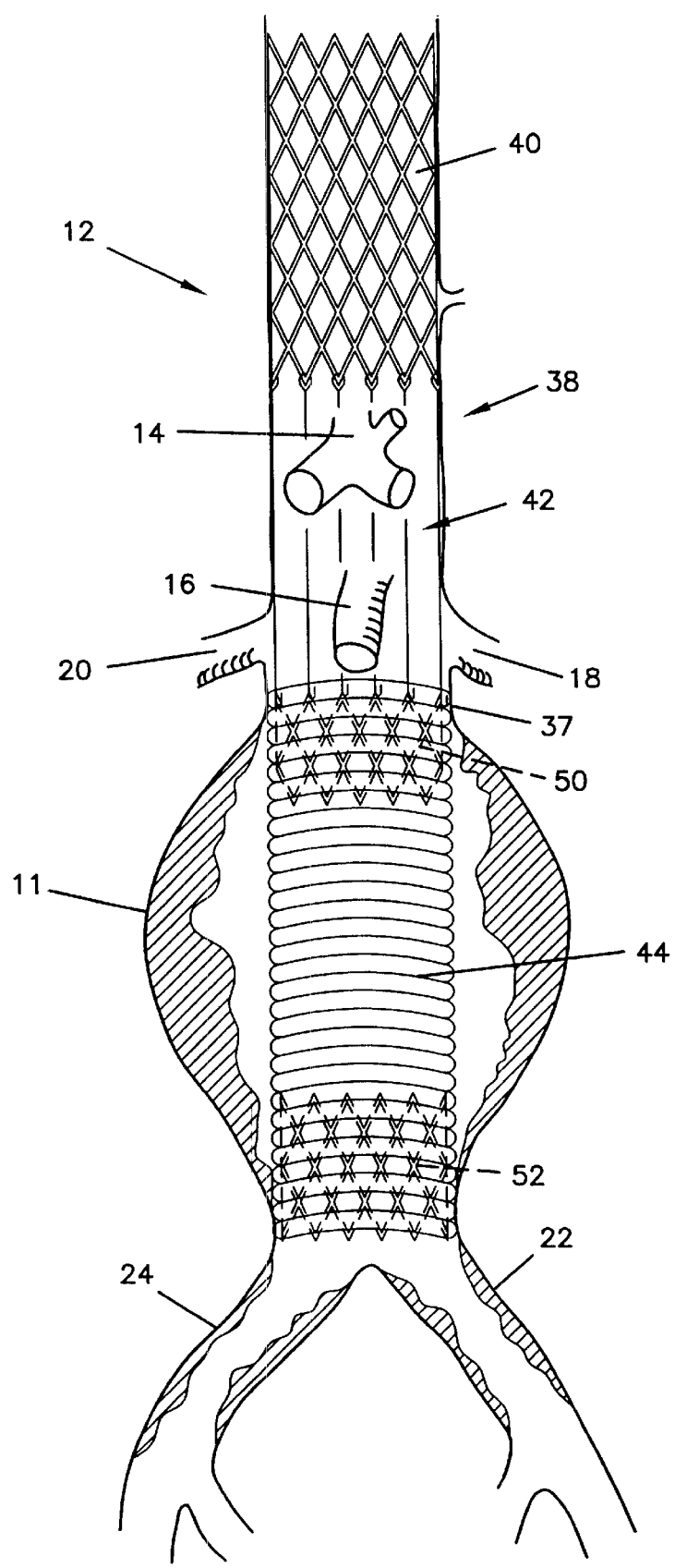
FIG. 5 is a pictorial diagram showing the prosthesis of FIG. 3 installed in a short-neck aneurysmal abdominal aorta in accordance with certain aspects of the invention.

FIG. 5, for example, depicts one preferred way of implanting the prosthesis 38 to repair an abdominal aortic aneurysm 11 with a short neck 37. The graft 44 is positioned within the aneurysm 11, with the graft's upper end positioned just below the orifices of the renal arteries 18, 20. The stent 40 is positioned within the lumen of the aorta 12 above the coeliac artery 14, commonly referred to as the supracoeliac portion of the aorta. This segment of the aorta is much less frequently diseased and it has a much smoother lumen than the segment below the renal arteries 18,20. It is much less likely to be heavily calcified or lined by irregular soft plaque and thrombus. Hence, the stent 40 can be more effectively affixed to this portion of the aorta.

The connecting wires 42 pass through the portion of the aorta 12 from which the coeliac, mesenteric and renal arteries 14, 16, 18 and 20 originate. The wires 42 allow blood to flow between the aorta 12 and the coeliac, mesenteric and renal arteries, i.e., without obstructing or occluding these arteries. The wires are preferably long enough to at least span the short segment of the aorta from which the coeliac, mesenteric and renal arteries originate so that neither the stent 40 nor the graft 44 obstructs these arteries.

The following are materials that are used to construct one preferred embodiment of the prosthesis; other materials can also be used. The tubular graft 44 is preferably formed of a collapsible plastic fabric such as a Dacron™ or e-PTFE (e.g., Gore Tex™) fabric; such grafts are known in the art. As one alternative, the graft 44 could be constituted by a self-expandable nitinol wire framework covered externally or lined internally by a very thin layer of Dacron™ or e-PTFE, as has recently become known in the art. Also as has recently become known in the art, the graft 44 can be either a single unit or a modular device consisting of two or more parts which can be inserted separately.

The connecting wires 42 are preferably constructed of a tin, flexible metal, such as stainless steel, titanium or nitinol. The wires are sufficiently thin so that they will not obstruct blood flow into the coeliac, mesenteric or renal arteries, and the wires are nonthrombogenic, i.e., they do not incite clot formation. The connecting wires 42 allow the apparatus to be implanted without regard to the rotational orientation of the apparatus about a longitudinal axis of the aorta. Such wires have been successfully used in the Greenfield vena cava filter for 10–20 years. In one preferred embodiment, 6 to 10 wires 42 are placed at regular intervals around the circumference of the stent 40 and graft 44; other numbers of wires could also be used. The wires 42 are connected to the stent 40 and graft 44 by, for example, loops or semi-closed hooks formed at the ends of the wires 42. Altenatively, fine, flexible monofilament polypropylene could be used in place of the metal wires 42. Like the wires, the polypropylene filaments would be of such fine caliber that they will not obstruct the coeliac 14, mesenteric 16 or renal 18, 20 arteries, so that they can be spaced around the entire 360 degree circumference of the upper stent 40 and graft 44. Alternatively, to further reduce the risk of obstruction of or embolization into these arteries, which originate from the anterior wall of the aorta (i.e., from the anterior 180 degrees in a cross-sectional plane), the wires or polypropylene filaments could be limited to the posterior 180–210 degrees of the circumferences of the upper stent 40 and graft 44.

Alternatively, to further reduce the risk of obstruction of or embolization into these arteries, which originate from the anterior wall of the aorta (i.e., from the anterior 180 degrees in a cross-sectional plane), the wires or polypropylene filaments could be limited to the posterior 180–210 degrees of the circumferences of the upper stent 40 and graft 44.

The stent 40 is preferably formed of stainless steel, titanium or nitinol. The stent 40 is expandable, but once expanded cannot be easily contracted so that the expanded stent maintains pressure against the inner wall of the aorta 12. Such stents are known in the art. In one preferred embodiment, the stent 40 is approximately three to four centimeters in length. However, various dimensions for the stent 40, wires 42, and graft 44 can be used, and the dimensions can be varied depending on the application of the prosthesis and the patient's dimensions. The stent 40 is depicted as a balloon-expandable stent. However, a nitinol self expanding stent, as is known in the art and does not require a balloon for expansion, could also be used. Such stents require a somewhat different delivery, system, as is known in the art.

The prosthesis 38 is in one preferred embodiment installed using an angioplasty catheter 34. The prosthesis is loaded onto a catheter 34 in collapsed form as shown in FIG. 4. The stent 40 in non-expanded form is placed over the collapsed balloon 32 of the catheter 34. The connecting wires 42 and graft 44 are compressed over the catheter 34 below the stent 40. The "collapsed" prosthesis 38 is preferably placed inside a flexible, plastic sheath 33 (e.g., Teflon™) for delivery into the iliac artery and aorta.

The prosthesis 38 offers another advantage over the, current endovascular prosthesis described above in the section titled "Description of Related Art." With that prosthesis, a tubular graft is placed over a catheter balloon and an expandable stent. The combined stent and graft over the balloon catheter creates a greater diameter of the combined prosthesis and balloon. With the greater diameter, it is more difficult to pass the device through the iliac arteries, which are often narrowed or tortuous. In contrast, with the preferred form of the present invention, the graft 44 is not positioned over the balloon and stent 40, but rather only over the catheter 34; the outer diameter of the device is therefore smaller.

The catheter 34 with the prosthesis 38 is passed into and positioned in the aorta 12 as follows. An incision is made in the right or left groin and a short cannula or "introducer" is inserted into either the common femoral or the external iliac artery. Under fluoroscopic control, a guide wire 30 is passed through the external iliac artery, the common iliac artery 22, 24, the aneurysm 11, and up into the supracoeliac aorta above the coeliac artery 14. Then, the catheter 34 bearing the collapsed prosthesis 38, placed inside a thin walled plastic delivery sheath 33 (e.g., Teflon™), is passed over the guide wire, through the same path, up into the supracoeliac aorta, also under fluoroscopic control.

When the stent 40 has been advanced just beyond the coeliac artery 14, the delivery sheath 33 is withdrawn and the balloon 32 is inflated to expand the stent 40 against the inner wall of the supracoeliac segment of the aorta, to secure the stent at that position. The balloon is then collapsed, freeing it from the stent, and the catheter 34 is withdrawn, leaving the prosthesis 38 positioned as shown in FIG. 5.

In one preferred embodiment, two additional expandable stents 50, 52 are used to further fix the graft 44. These stents 50, 52 are shown in broken lines in FIG. 5. The construction of the stents 50, 52 can be generally the same as that of the stent 40 positioned at the supracoeliac aorta. However, the stents 50, 52 are preferably shorter than the stent 40. The stent 50 is used to press the upper end of the graft 44 against the inner wall of the neck 37 of the aneurysm, so as to obstruct blood flow outside of the graft through the aneurysm 11. The stent 52 is used to press the lower end of the graft 44 against the inner wall of the aorta just below the aneurysm 11.

In one preferred embodiment, the stents 50, 52 are successively positioned using a balloon catheter 34 in manner similar to the positioning of the prosthesis 38 with the stent 40. The stent 50, in non-expanded form, is placed over a collapsed balloon 32 of a catheter 34. The catheter 34, bearing the stent 50 placed inside a sheath 33 (e.g., Teflon™), is passed over the guide wire 30 into the aorta 12 through the graft 44 and positioned at the neck 37 of the aneurysm 11, just below the line of attachment of the connecting wires 42. The sheath 33 is then withdrawn and the balloon 32 expanded to expand the stent 50 as shown in FIG. 5. This stent 50 helps to maintain the graft 44 in cylindrical conformation and expanded against the aortic wall to prevent blood flow outside the graft into the aneurysm. The catheter 34 is then withdrawn. While the stent 50 is sufficient to maintain the graft 44 open and to help prevent leaks, it would generally be insufficient by itself to adequately anchor the graft 44 and prevent distal migration of the graft 44 in patients who have a short aneurysm neck 37, as is common.

The stent 52, in non-expanded form, is placed over a balloon 32 of a catheter 34 and is installed in a similar manner. The stent 52 is positioned at the lower portion of the graft 44 to help seal the graft against the wall of the distal aorta, as shown in FIG. 5. Alternatively, if the aneurysm 11 extends to the iliac arteries so that the stent 52 cannot be satisfactorily fixed to the distal aorta, the graft 44 can be dimensioned to extend into the right or left iliac artery 22, 24 and the stent 52 fixed there at the iliac artery. In this case, the opposite iliac artery is permanently occluded by a catheter-placed endoluminal device and a crossover vascular graft performed between the right and left external iliac arteries, or the common femoral arteries, to maintain blood flow to the opposite leg, as is sometimes done with current prostheses and as is known in the art.

Further as is sometimes done with current prostheses and as is known in the art, in another alternative, an "inverted Y" bifurcated graft is used. The second limb of the graft is "snared" by a catheter advanced through the contralateral iliac artery and the end of this limb is pulled down into the contralateral iliac artery and secured with a fourth stent. In this embodiment, a crossover vascular graft is not needed.

Figure 6A:
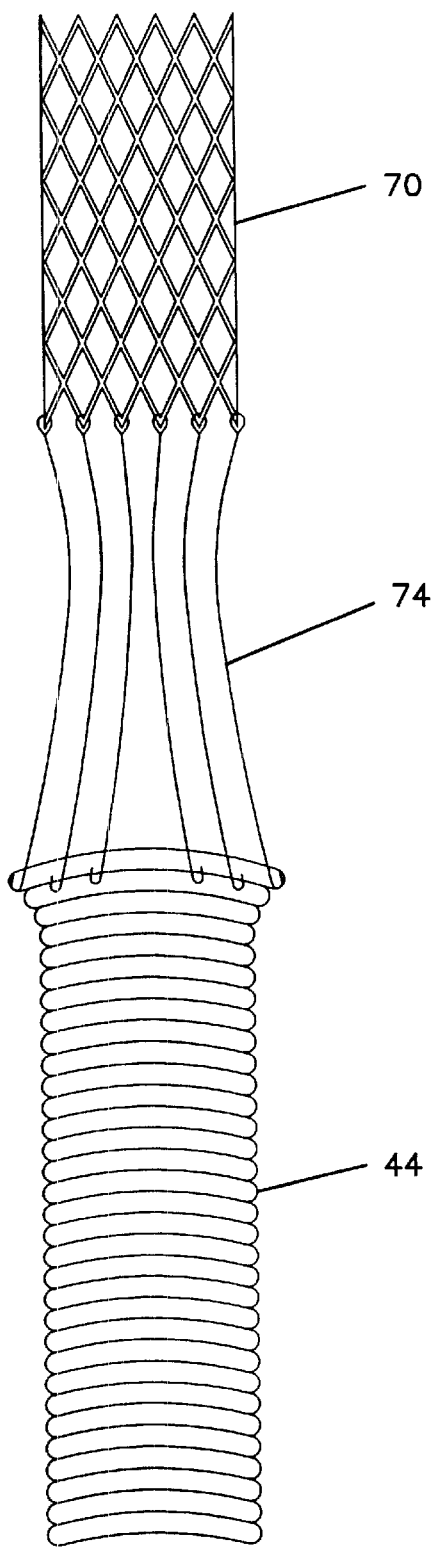
FIGS. 6a and 6b are pictorial diagrams showing other embodiments of the prosthesis provided by the invention.

Another embodiment of the invention is illustrated in FIG. 6a. In this embodiment, a metal stent 70 is connected to the graft 72 by thin, elastic metal wires 74 that, from the stent, curve radially, first inward and then outward. The wires 74 are, at one end, rigidly attached to the lower end of the stent 70 and, at their other end, are attached to the upper end of the graft 44, so that the lower ends of the extensions 74 press radially outward. The wires 74 are dimensioned so that they extend from the aneurysm neck 37 to above coeliac arteries 14 (not shown in FIG. 6a). When the delivery sheath 33 is pulled back, these wires 74 press the upper end of the graft 44 against the neck of the aneurysm, to help seal the graft against the aneurysm neck. With this embodiment, a stent 50 may not be necessary at the neck of the aneurysm, as the outward pressure of the wires 74 would in most cases be sufficient to seal the upper end of the graft against the aneurysm neck 37. However, this embodiment of the invention does not preclude the use of a stent 50 at the upper end of the graft 44.

Figure 6B:
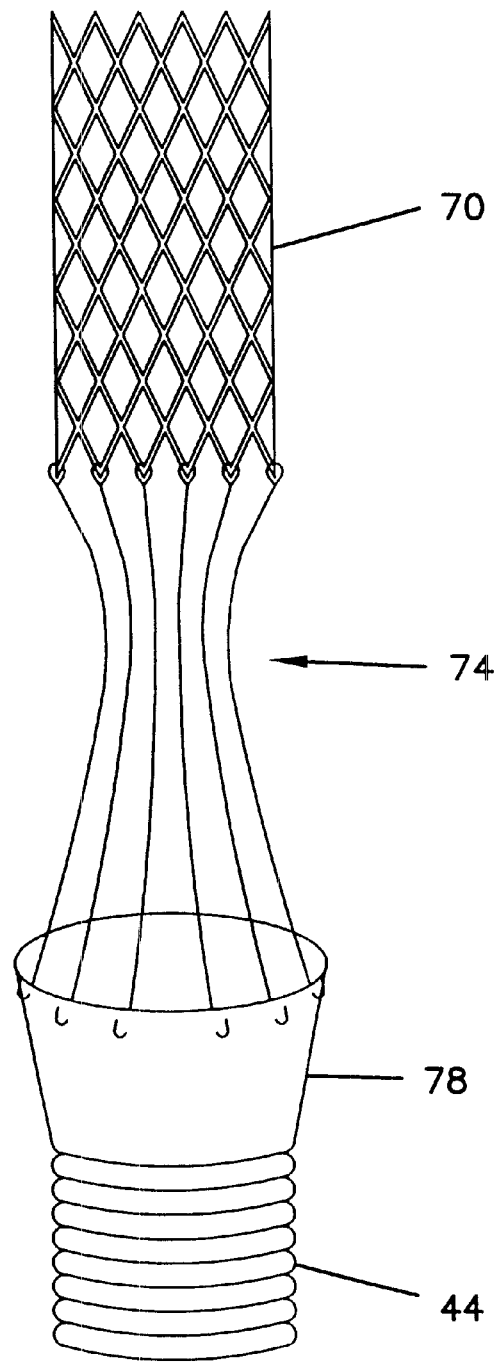

Because the wires 74 press radially outward independent of one another, the wires can extend to conform to the shape of an irregularly-shaped (e.g., not perfectly cylindrical) aneurysm neck 37, thereby improving the seal. To take advantage of this, as indicated in FIG. 6a, the upper end of the graft 44 to which the wires 74 are attached preferably readily stretches circumferentially, so that the upper end can conform to an irregularly-shaped aneurysm neck under the pressure of the wires 74. In one preferred embodiment, depicted in FIG. 6b, the circumferentially stretchable upper end 78 is one to two centimeters wide (measured along the graft's longitudinal axis). A suitable material for the upper end 78 is e-PTFE fabricated to stretch circumferentially, as will be recognized by those skilled in the art. (Tubular grafts of e-PTFE fabricated to stretch longitudinally exist and are used for open or trans-abdominal repair of abdominal aortic aneurysms.)

Figure 7A:
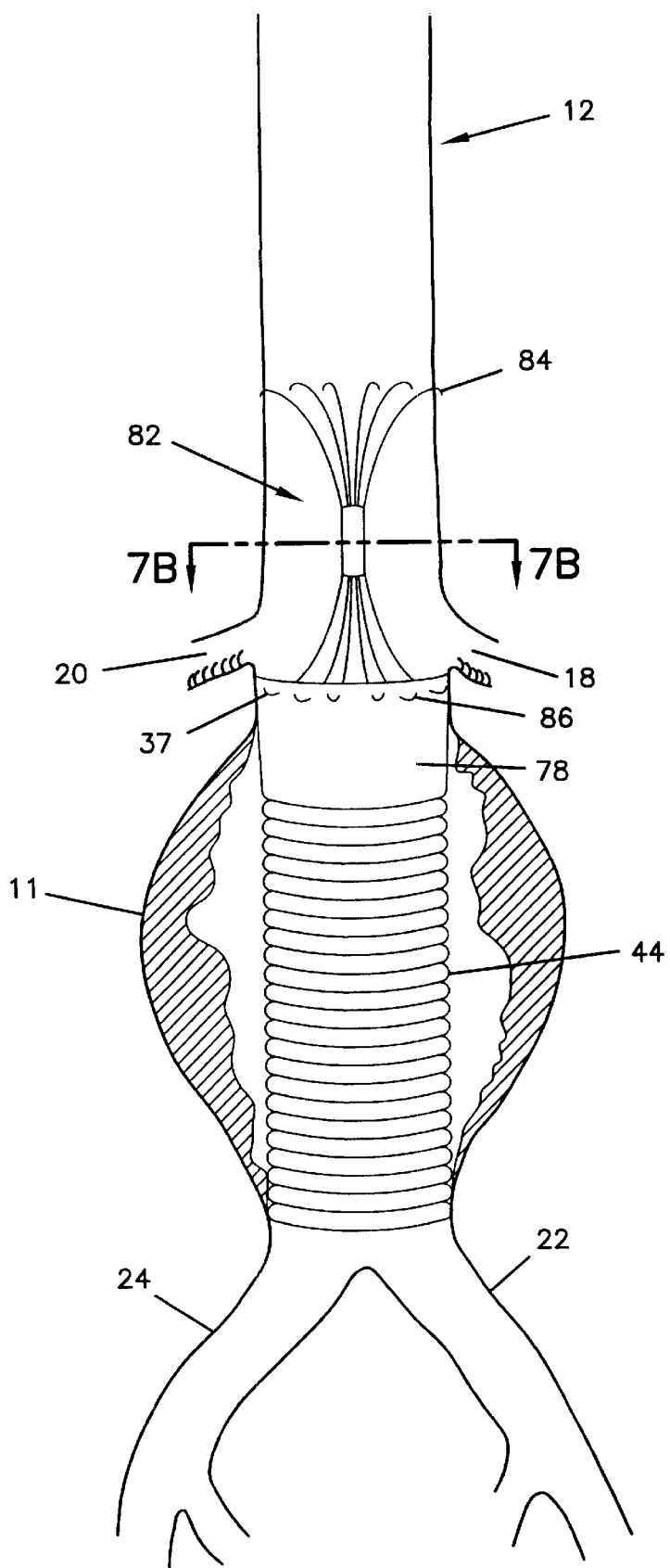
FIG. 7a is pictorial diagram showing another embodiment of the prosthesis provided by the invention installed in a short-neck aneuryzmal abdominal aorta.

FIG. 7a illustrates another embodiment of the invention, in which the stent 40 and connecting wires 42 are replaced by a single unit 82 composed of thin, pre-curved, elastic wires that are joined together near their mid-sections and, from their mid-sections, curve radially outward. The wires of the unit 82 are compressed together when loaded into a delivery catheter sheath or cartridge and spring out radially once released from the sheath or cartridge. The upper ends 84 of the wires have sharp angled end points that function as prongs that embed in the supracoeliac aortic wall to secure the unit 82. The lower ends 86 are attached to the upper end of the graft 44 by small rings or hooks. The lower ends 86 press out radially, independently of each other to seal the graft 44 against the aneurysm neck 37. As a result, the ends of the unit 82 can conform to an irregular (e.g., non-cylindrical) surface, as illustrated in cross-sectional plane view in FIG. 7b.

Figure 7B:
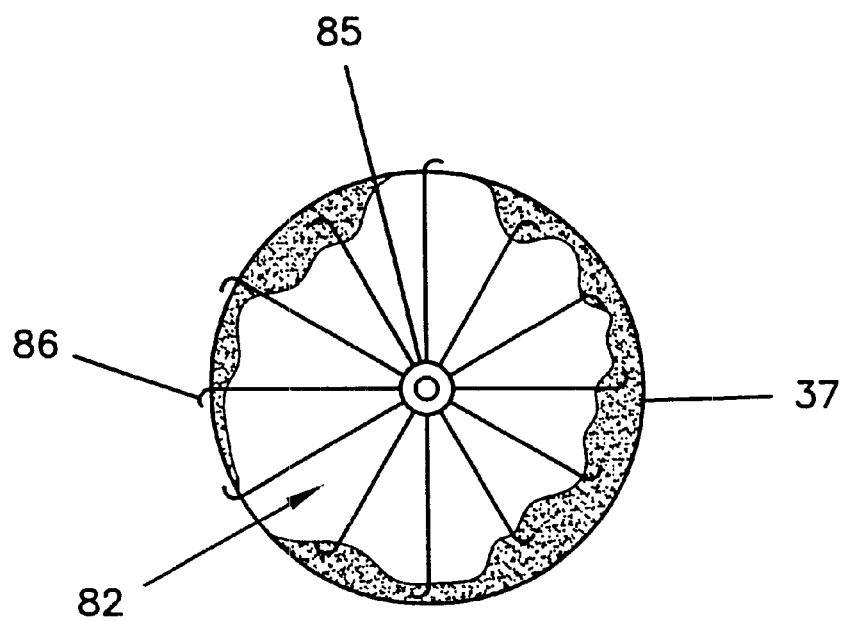

The unit 82 is dimensioned so that the wires extend from the aneurysm neck 37 to above coeliac arteries 14 (not shown in FIG. 7a). In one preferred embodiment, the wires are formed of curved stainless steel or titanium wires that are welded together near their mid-sections. Also in one preferred embodiment, the upper end 78 of the graft 44 is formed to be circumferentially stretchable, as described with respect to FIGS. 6a and 6b. Furthermore, as illustrated in FIG. 7b, in one preferred embodiment the midsection of the unit 82 has a central lumen 85 for a guide wire for use in delivering the prosthesis. A modified delivery system may be required for the delivery and positioning of this prosthesis. A stent 52 (not shown) may also be used for securing the lower end of the graft 44, as described with respect to FIG. 5.

Figure 8:
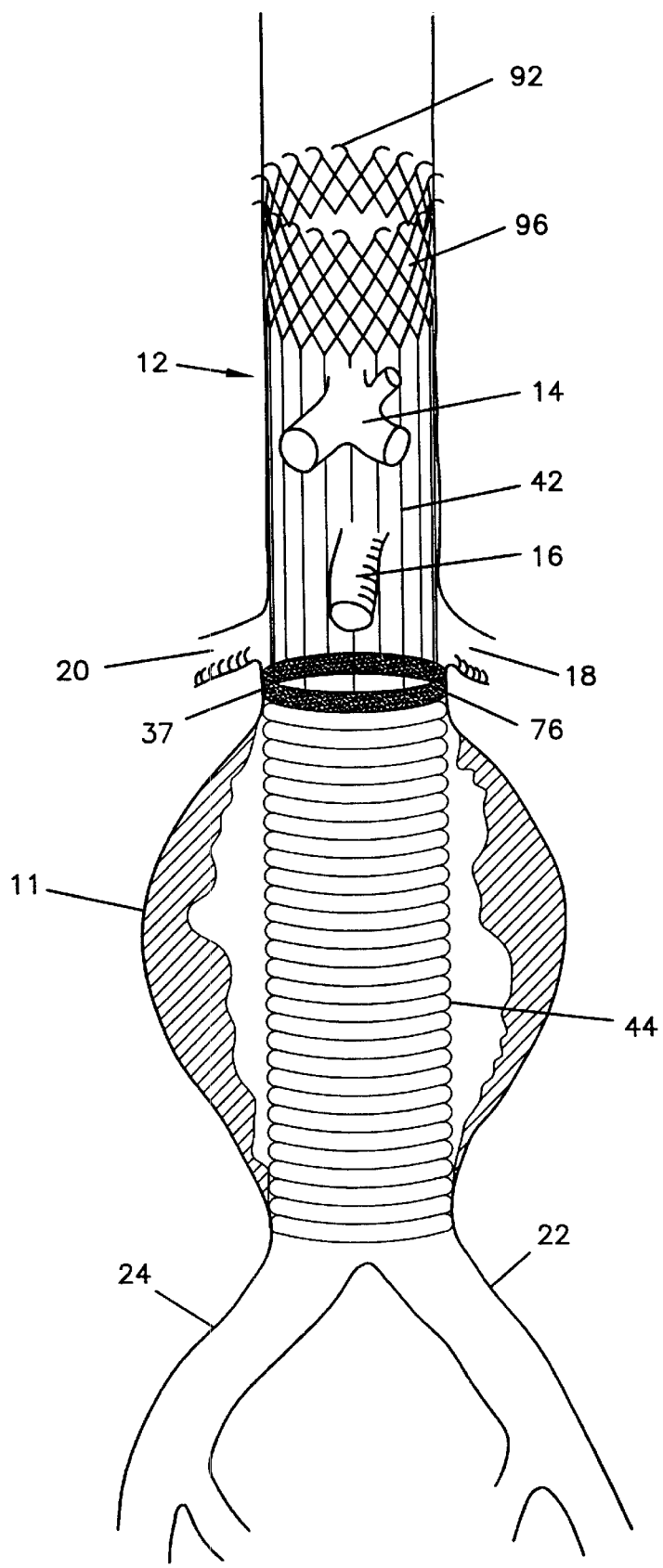
FIG. 8 is pictorial diagram showing another embodiment of the prosthesis provided by the invention installed in a short-neck aneurysmal abdominal aorta.

FIG. 8 illustrates yet another embodiment of the invention in which the graft 44 is modified by the addition of a collar 76 of highly compressible, elastic material at the upper end of the graft 44. The collar 76 is preformed to expand radially once the delivery sheath 33 is pulled back, to help seal or close any small spaces between the graft and the neck of the aneurysm 37. In one preferred embodiment, the collar 76 is approximately one centimeter wide (measured along the graft's longitudinal axis) and is joined to the graft 44 above the line of attachment of the connecting wires 42 to the graft 44. Examples of materials that could be used for the collar 76 include very loosely knitted or velour Dacron™, highly porous e-PTFE or Teflon™ "felt." The highly compressible, elastic collar 76 could also be added to the upper end of the circumferentially stretchable upper end of the graft 44 that is described with respect to FIGS. 6a and 6b, to further improve the seal to an irregular aneurysm neck 37.

Within the scope of the invention, various further changes can be made to the embodiments described above. For example, the expandable stent 40 can be replaced with an expandable ring of small metal hooks, which can be "fired" into the inner wall of the aorta with a balloon catheter using distention of the balloon to drive the hooks into the aortic wall. Also, the expandable stents 40 and 70 (shown in FIGS. 5 and 6) can be modified by the addition of small metal barbs to the outer surface of the stent to help secure the stents to the aortic wall and prevent downstream migration. For example, FIG. 8 shows an expandable stent 90 having elastic metal barbs 92 at the upper end of the stent 90. The barbs 92 can be compressed when covered by the delivery sheath 33 and then spring radially outward when the delivery sheath 33 is withdrawn. The barbs 92 preferably have sharp ends which embed into the wall of the supracoeliac aorta.

Furthermore, while the invention has been illustrated for the repair of abdominal aortic aneurysms, the invention might be used to repair other aortic aneurysms, e.g., certain thoracic aortic aneurysms.

Therefore, it is to be understood that the foregoing description of exemplary embodiments of the invention has been presented for the purposes of illustration and description. It is not intended to be exhaustive or to limit the invention to the precise forms disclosed. Many further modifications and variations are possible in light of the above teaching. The scope of the invention is not to be limited to this detailed description, but rather by the claims appended hereto.

What is claimed is:

1. An apparatus for repairing an aneurysm of an aorta, the aorta including a region from which celiac, mesenteric and renal arteries originate, the aneurysm being located along a section of the aorta positioned between the renal and iliac arteries, the apparatus including:

a) a tube to serve as a conduit for blood flow in the aneurysm of the aorta, the tube being dimensioned in length to at least extend a length of the aneurysm and to terminate below the renal arteries;

b) an anchor, separated by a distance from the tube, to secure the apparatus within the aorta; and c) a plurality of thin lines interconnecting the anchor and the tube, the lines being dimensioned to a length greater than a length of the region of the aorta from which the celiac, mesenteric and renal arteries originate, each of the lines being sufficiently thin so as to not obstruct blood flow to the celiac, mesenteric and renal arteries, the plurality of thin lines including more than 2 thin lines.

2. The apparatus of claim 1, wherein tile plurality of lines art flexible metal wires.

3. The apparatus of claim 1, wherein the plurality of lines are flexible monofilament.

4. The apparatus of claim 1, wherein the plurality of lines are evenly distributed about the circumference of the tube.

5. The apparatus of claim 1, wherein the plurality of lines curve radially outward at a first end of the tube to which the lines are connected, to push the fir end of the tube against an aortic wall.

6. The apparatus of claim 5, wherein the first end of the tube is circumferentially stretchable, so that the end of the tube can conform to the shape of an aortic wall.

7. The apparatus of claim 1, wherein the tube includes a collar of compressible, elastic material at a first end of the tube to which the plurality of lines are attached wherein the collar expands radially to conform to an aortic wall.

8. The apparatus of claim 1, wherein the anchor is an expandable metal stent.

9. The apparatus of claim 1, wherein the apparatus includes 6–10 thin lines.

10. The apparatus of claim 1, wherein the apparatus includes at least 6 thin lines.

11. The apparatus of claim 1, wherein the apparatus can be implanted without regard to the rotational orientation of the apparatus about a longitudinal axis of the aorta.

12. A method for repairing an aneurysm of an aorta, the aorta including a region from which celiac, mesenteric and renal arteries originate, the aneurysm being located along a section of the aorta positioned between the renal and iliac arteries, the method comprising:

A) providing an apparatus including:
    a) a tube to serve as a conduit for blood flow in the aneurysm of the aorta, the tube being dimensioned in length to at least extend a length of the aneurysm;
    b) an anchor, separated by a distance from the tube, to secure the apparatus within the aorta; and
    c) a plurality of thin lines interconnecting the anchor and the tube, the lines being dimensioned to a length greater than a length of the region of the aorta from which the celiac, mesenteric and renal arteries originate, each of the lines being sufficiently thin so as to not obstruct blood flow to the celiac, mesenteric and renal arteries, the plurality of thin lines including more than 2 thin lines; and B) implanting the apparatus in the aorta with an uppermost portion of the tube terminating below the renal arteries and the anchor secured above the celiac artery.

13. The method of claim 12, wherein the apparatus can be implanted without regard to the rotational orientation of the apparatus about a longitudinal axis of the aorta.

* * * * *

UNITED STATES PATENT AND TRADEMARK OFFICE
CERTIFICATE OF CORRECTION

PATENT NO. : 6,669,720 B1
DATED : December 30, 2003
INVENTOR(S) : Pierce

Page 1 of 1

It is certified that error appears in the above-identified patent and that said Letters Patent is hereby corrected as shown below:

Column 1,
Line 22, "related toga high" should read -- related to a high --

Column 5,
Lines 6-7, "of a tin, flexible" should read -- of a thin, flexible --.
Line 53, "delivery, system," should read -- delivery system, --
Line 64, "over the," should read -- over the --

Column 9,
Lines 19-20, "wherein tile plurality of lines art flexible" should read
-- wherein the plurality of lines are flexible --
Line 22, "flexible monofilament." should read -- flexible monofilaments. --
Line 27, "push the fir end" should read -- push the first end --
Line 35, "attached wherein" should read -- attached, wherein --

Signed and Sealed this

Twenty-sixth Day of October, 2004

JON W. DUDAS
*Director of the United States Patent and Trademark Office*